US006444217B1

(12) United States Patent
Kwok et al.

(10) Patent No.: US 6,444,217 B1
(45) Date of Patent: Sep. 3, 2002

(54) DRUG DELIVERY DEVICES, AND METHODS OF USE

(75) Inventors: Connie Sau-Kuen Kwok; Buddy D. Ratner; Pierre D. Mourad; Lawrence A. Crum, all of Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 09/844,659

(22) Filed: Apr. 25, 2001

Related U.S. Application Data
(60) Provisional application No. 60/199,577, filed on Apr. 25, 2000.

(51) Int. Cl.[7] .............................. A61F 2/02; A61L 15/16; A61K 9/16; A61K 47/30
(52) U.S. Cl. ........................ 424/423; 424/447; 424/486; 514/772.3
(58) Field of Search .............................. 424/423, 447, 424/486; 514/772.3

(56) References Cited

U.S. PATENT DOCUMENTS 5,811,151 A * 9/1998 Hendriks et al. .......... 427/2.24

OTHER PUBLICATIONS

Whiteside, G.M. et al., "Organic Chemistry in Two Dimensions: Surface–Functionalized Polymers and Self–Assembled Monolayer Films," *Chemtracts–Organic Chemistry,* 1:171–187, 1988.
Kwok, C.S et al, "Surface Modification of Polymers with Self–assembled Molecular Structures: Multitechnique Surface Characterization," *Biomacromolecules* 2000, 1:139–148 (2000).
Kwok, C.S., et al., "Modification of Polymer Surfaces with Self–Assembled Monolayers," *Society of Biomaterials Meeting,* Providence, RI, (poster) Apr. 28–May 2, 1999.
Ulman, A., *Chem. Rev.,* 96:1533–54 (1996).
Bain, C.D. et al., *J. Am. Chem. Soc.,* 111:321–34 (1989).
Sagiv, J., *J. Am. Chem. Soc.,* 102:92–98 (1980).
Maoz, R. et al., *J. Chim Phys.,* 85:1059–65 (1988).
Song, Y.P. et al., *Langmuir,* 8:257–61 (1992).
Charych, D.H., *MRS Bull.,* 17:61–66 (1992).
Sagiv, J., *Isr. J. Chem.,* 18:339–46 (1979).
Maoz, R. eta l., *Langmuir,* 3:1034–44 (1987).
Maoz, R. et al., *Supramol. Sci.,* 2 (1995).
Bohme, P. et al., *Langmuir,* 15:5323–28 (1999).
Chaudhury, M., *Biosens, Bioelectron.,* 19:785–88 (1995).
Ferguson, G.S. et al., *Macromolecules* 26:5870–75 (1993).
Cheng, S.S. et al., *Langmuir,* 11:1190–95 (1995).
Silver, J.H. et al., *J. Biomed. Mater. Res.,* 28:535–48 (1995).

* cited by examiner

*Primary Examiner*—Carlos Azpuru
(74) *Attorney, Agent, or Firm*—Christensen O'Connor; Johnson Kindness PLLC

(57) ABSTRACT

The present invention provides biomedical devices, such as implantable drug delivery devices that possess a surface layer adapted to retain, and controllably release, drug molecules for administration to a subject. The present invention also provides methods of delivering a drug to a subject, the methods utilizing biomedical devices of the invention.

17 Claims, 11 Drawing Sheets

DRUG DELIVERY DEVICES, AND METHODS OF USE

CROSS-REFERENCE TO RELATED APPLICATION

This application claims benefit of priority from U.S. Provisional Patent Application No. 60/199,577, filed Apr. 25, 2000, under 35 U.S.C. 119.

GOVERNMENT RIGHTS

This invention was funded in part by the National Science Foundation, Grant No. NSF EEC 9529161. The United States Government may have certain rights in this invention.

FIELD OF THE INVENTION

This invention relates to drug release compositions, and to implantable medical devices that include a surface layer adapted to controllably release a drug in response to sound or thermal energy.

BACKGROUND OF THE INVENTION

When a biomedical device is implanted into the human body, cells come in contact with the surface of the device and may trigger an adverse foreign body reaction in response to chemical and physical properties of the device surface. Surfaces with defined chemical and physical characteristics are therefore needed to improve the biocompatibility of implanted materials. Moreover, there is a continuing need for drug delivery devices that can be implanted into a living body, such as a mammalian body, and that controllably release one or more drugs within the body. It is particularly desirable that drug delivery devices are capable of delivering several defined drug dosages at desired intervals over a period of days, months or years.

In one embodiment the present invention provides implantable medical devices that possess a surface layer adapted to retain, and controllably release, drug molecules for administration to a subject in need thereof. Biologically active molecules can be covalently attached to the surface layer of some embodiments of the biomedical devices of the invention, for example to reduce or eliminate an adverse foreign body reaction to an implanted medical device, or in any situation where it is desirable to immobilize a molecule, such as a biological polymer, as more fully discussed herein.

SUMMARY OF THE INVENTION

In one aspect, the present invention provides biomedical devices comprising: (a) a polymeric or hydrogel substrate; and (b) a surface layer comprising a multiplicity of $C_{10}$ to $C_{22}$ unbranched alkyl molecules, wherein: (1) the multiplicity of alkyl molecules define a multiplicity of spaces therebetween; (2) each member of the multiplicity of alkyl molecules possesses a proximal end and a distal end, the proximal end being covalently linked to the substrate; and (3) the surface layer has an ordered state and a less ordered state, the surface layer being reversibly convertible to the less ordered state from the ordered state in response to an effective amount of sound or thermal energy.

In some embodiments, devices of the invention further include drug molecules disposed within the substrate and also disposed in the spaces between the $C_{10}$ to $C_{22}$ unbranched alkyl molecules. These embodiments of the devices of the invention are useful, for example, as implantable drug delivery devices.

In other embodiments, the devices of the invention further include a proreactive chemical groups covalently attached to distal ends of the $C_{10}$ to $C_{22}$ alkyl molecules. Proreactive chemical groups permits attachment of effector molecules after deblocking of the proreactive chemical group.

In other embodiments, the devices of the invention further include effector molecules covalently attached to distal ends of the $C_{10}$ to $C_{22}$ alkyl molecules.

By way of non-limiting example, embodiments of the devices of the invention that include proreactive chemical groups or effector molecules can be utilized in applications where biological signals or trigger molecules are needed at the surface of implanted medical devices to improve tissue healing and biocompatibility.

In another aspect, the present invention provides methods of making a biomedical device, the methods comprising the steps of: (a) disposing a multiplicity of drug molecules within a polymeric or hydrogel substrate; and (b) covalently attaching a multiplicity of $C_{10}$ to $C_{22}$ unbranched alkyl molecules to the substrate by forming a covalent linkage between an end group on each member of the multiplicity of $C_{10}$ to $C_{22}$ unbranched alkyl molecules and a reactive group on the substrate, thereby forming a surface layer on the substrate wherein: (1) the multiplicity of alkyl molecules define a multiplicity of spaces therebetween; (2) each member of the multiplicity of alkyl molecules possesses a proximal end and a distal end, the proximal end being covalently linked to the substrate; and (3) the surface layer has an ordered state and a less ordered state, the surface layer being reversibly convertible to the less ordered state from the ordered state in response to an effective amount of sound or thermal energy.

In yet another aspect, the present invention provides methods of delivering a drug to a subject, the methods comprising the steps of: (a) introducing into a subject a device comprising: (1) a polymeric or hydrogel substrate comprising a multiplicity of drug molecules; and (2) a surface layer comprising a multiplicity of $C_{10}$ to $C_{22}$ unbranched alkyl molecules, wherein: (i) the multiplicity of alkyl molecules define a multiplicity of spaces therebetween; (ii) a multiplicity of drug molecules are disposed within the spaces; (iii) each member of the multiplicity of alkyl molecules possesses a proximal end and a distal end, the proximal end being covalently linked to the substrate; and (iv) the surface layer has an ordered state and a less ordered state, the surface layer being reversibly convertible to the less ordered state from the ordered state in response to an effective amount of sound or thermal energy; and (b) subjecting the device to an amount of sound or thermal energy effective to induce release of the drug molecules from the surface layer.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Unless specifically defined herein, all terms used herein have the same meaning as they would to one skilled in the art of the present invention.

As used herein, the term "biomedical device" refers to a device that is used to deliver a biologically active molecule to a living subject, or to measure the level of a biologically active molecule, or to detect the presence of a biologically active molecule.

As used herein, the term "layer" refers to a layer of molecules (such as a single layer of $C_{10}$ to $C_{22}$ unbranched alkyl molecules) covalently attached to a polymeric or hydrogel substrate. The molecules that form the layer may or may not be evenly distributed throughout the layer. The surface of the substrate to which the layer is attached may not be flat, and so the molecules within the layer may not all be at the same height relative to each other. Moreover, the layer may extend into the substrate in the portion of the substrate close to the substrate surface. Typically, the surface layer does not penetrate the substrate surface to a depth of greater than 1 $\mu$m.

As used herein, the term "effector molecule" refers to a molecule that effects a function on the surface of a device of the invention (e.g., reduces the foreign body reaction of a living subject into which a device of the invention is implanted). For example, polyethylene glycol oligomers can be utilized as effector molecules to reduce non-specific absorption of protein to an implanted medical device of the invention.

As used herein, the term "implantable medical device" refers to a device that is completely or partially implanted into an animal body (such as a human body) during the course of normal operation of the device.

In one embodiment, the present invention provides biomedical devices comprising: (a) a polymeric or hydrogel substrate; and (b) a surface layer comprising a multiplicity of $C_{10}$ to $C_{22}$ unbranched alkyl molecules, wherein: (1) the multiplicity of alkyl molecules define a multiplicity of spaces therebetween; (2) each member of the multiplicity of alkyl molecules possesses a proximal end and a distal end, the proximal end being covalently linked to the substrate; and (3) the surface layer has an ordered state and a less ordered state, the surface layer being reversibly convertible to the less ordered state from the ordered state in response to an effective amount of sound or thermal energy.

Figure 1:
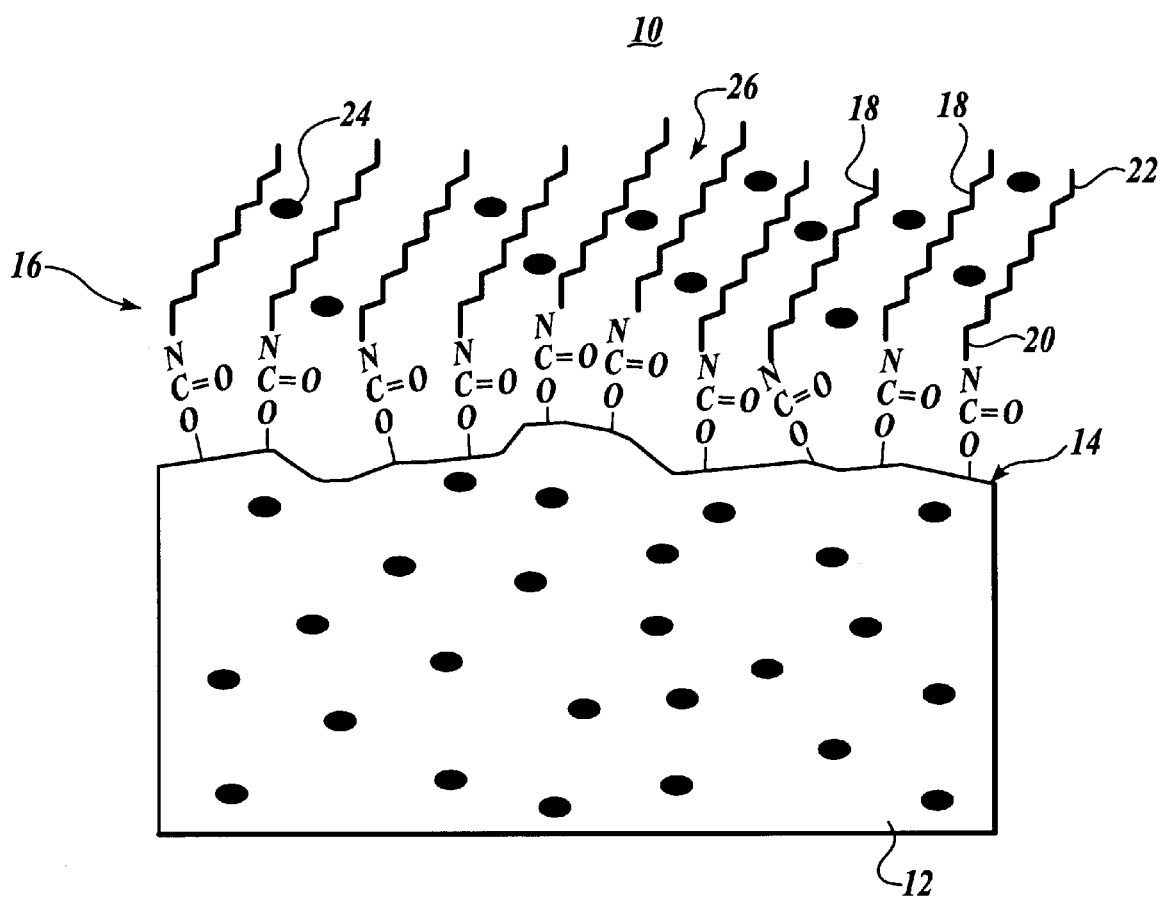
FIG. 1 shows a representative device of the present invention adapted for use as an implantable drug delivery device. The components of the device are not drawn to scale.

FIG. 1 shows a representative biomedical device 10 of the present invention including a substrate 12 (made from a polymer or hydrogel), including a substrate surface 14 and a surface layer 16 including a multiplicity of unbranched alkyl molecules 18 ($C_{12}$ molecules in the embodiment shown in FIG. 1). Each $C_{12}$ alkyl molecule 18 includes a proximal end 20 and a distal end 22. Proximal end 20 of each $C_{12}$ alkyl molecule 18 is covalently linked to substrate 12 by a urethane bond. In the embodiment shown in FIG. 1, device 10 includes drug a molecules 24 disposed within substrate 12 and also disposed in spaces 26 between molecules 18 of layer 16. In the embodiment shown in FIG. 2A, device 10 includes a proreactive chemical group 28 located on distal end 22 of molecules 18.

Proreactive chemical group 28 permits effector molecules 30 (shown in FIG. 2B) to be attached to molecule distal ends 22 after deblocking of proreactive chemical group 28. In the embodiment shown in FIG. 2B, device 10 includes effector molecules 30 covalently attached to distal end 22 of molecule 18. It is within the scope of the invention that the embodiments of device 10 shown in FIG. 2A and FIG. 2B include drug molecules 24 disposed within substrate 12, or within spaces 26, or within both substrate 12 and spaces 26.

Typically, molecules 18 of layer 16 are aligned side-by-side (such as shown in FIG. 1), although the density of molecules 18 may vary over polymeric substrate surface 14, and molecules 18 may not be vertically aligned with respect to substrate surface 14, but may be covalently attached to their point of attachment at an angle, such as an angle of approximately 33 degrees. Further, when substrate 12 is sufficiently porous to permit penetration of alkyl molecules 18, then layer 16 can extend into the portion of substrate 12 adjacent to substrate surface 14. Typically, layer 16 does not penetrate more than 1 μm into substrate 12 (i.e., typically few or no alkyl molecules 18 penetrate further than 1 μm from substrate surface 14 into substrate 12).

Representative devices 10 of the invention include implantable medical devices. Some implantable, medical devices are completely implanted into a living body (i.e., the entire device is implanted within a living body), while some implantable, medical devices are partially implanted into a body (i.e., only part of the device is implanted within a living body, the remainder of the device being located outside of the living body). Further, some implantable, medical devices include both living tissue and non-living material. Representative examples of implantable medical devices include, but are not limited to: prosthetic devices (such as artificial hip joints and artificial knee joints), cardiovascular devices (such as vascular grafts and stents), skin substitutes (such as dermal and epidermal scaffolds), scaffolds that support tissue growth (in such anatomical structures as bone, tooth, nerves, pancreas, eye and muscle), implantable biosensors (such as those used to monitor the level of drugs within a living body, or the level of blood glucose in a diabetic patient) and percutaneous devices (such as catheters) that penetrate the skin and link a living body to a medical device, such as a kidney dialysis machine. Examples of partially implanted medical devices include catheters and skin substitutes. Examples of medical devices that are completely implanted into a living body include stents and artificial hip joints.

Figure 2A:
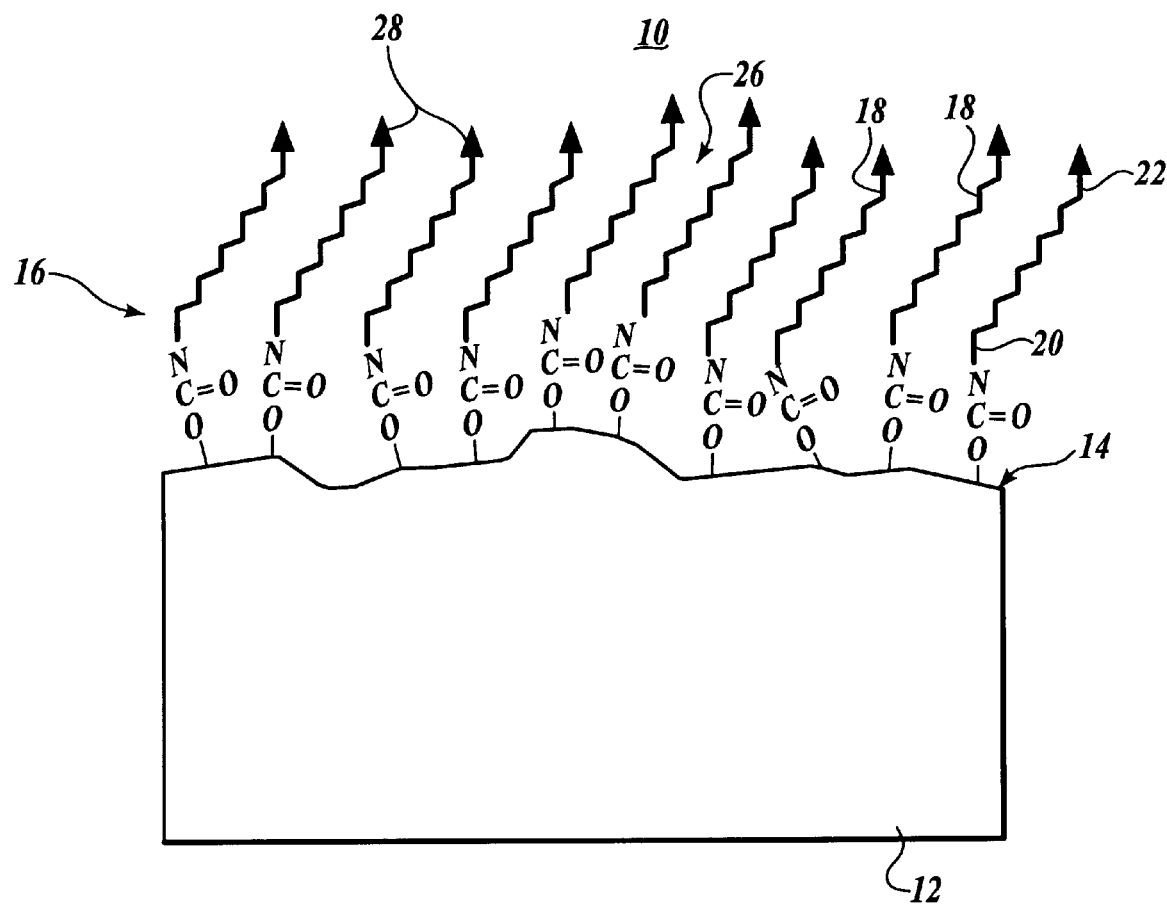
FIG. 2A shows a device of the present invention that includes proreactive chemical groups.
Figure 2B:
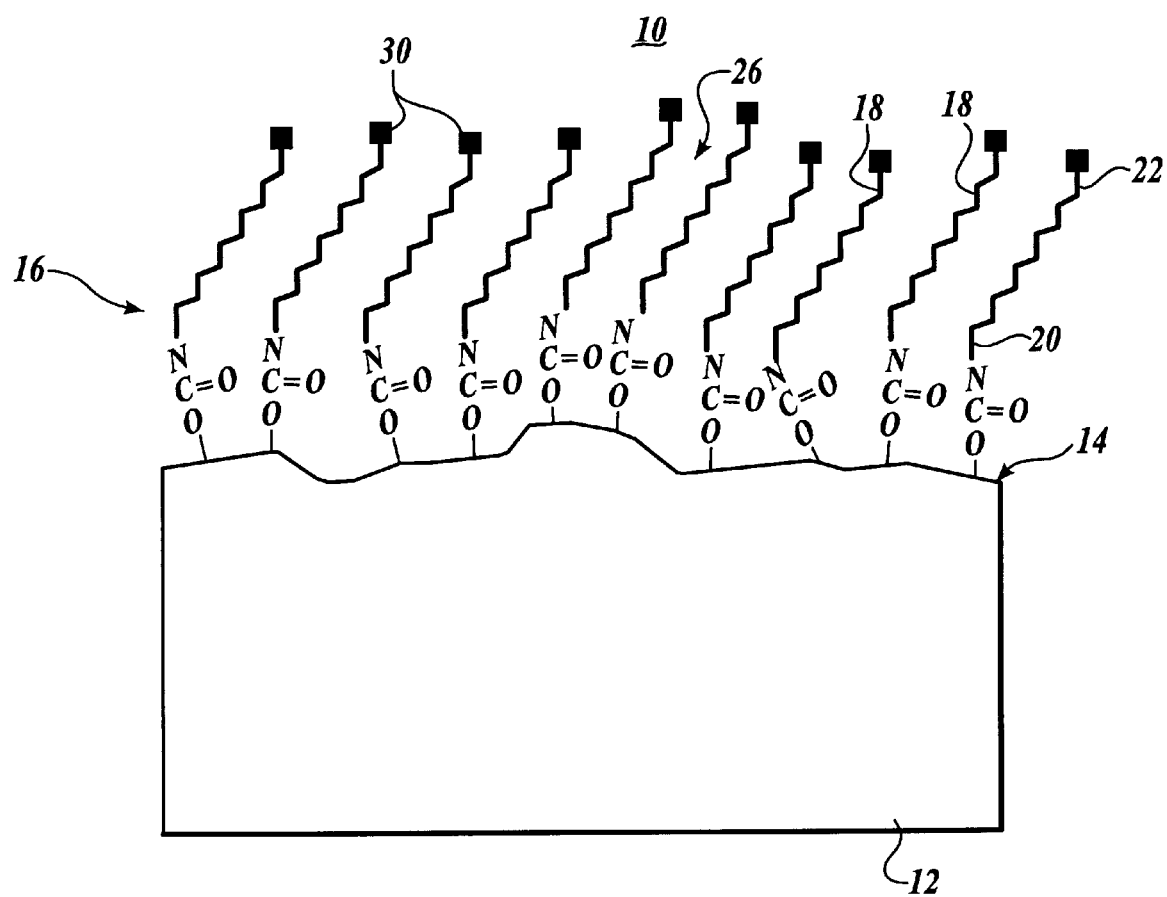
FIG. 2B shows a device of the present invention that includes effector molecules.

By way of non-limiting example, embodiments of device 10 that include proreactive chemical groups 28, such as the embodiment shown in FIG. 2A, or effector molecules 30, such as the embodiment shown in FIG. 2B, can be utilized in applications where biological signals or trigger molecules are needed at the surface of implanted medical devices to improve tissue healing and biocompatibility. Such examples include, but are not limited to, cardiovascular devices, such as stents and vascular grafts, to which appropriate molecules to induce cell growth or prevent thrombosis can be immobilized via proreactive chemical groups 28. Other examples include the immobilization of molecules to induce the vascularization and appropriate tissue integration of implanted biosensors.

Figure 3:
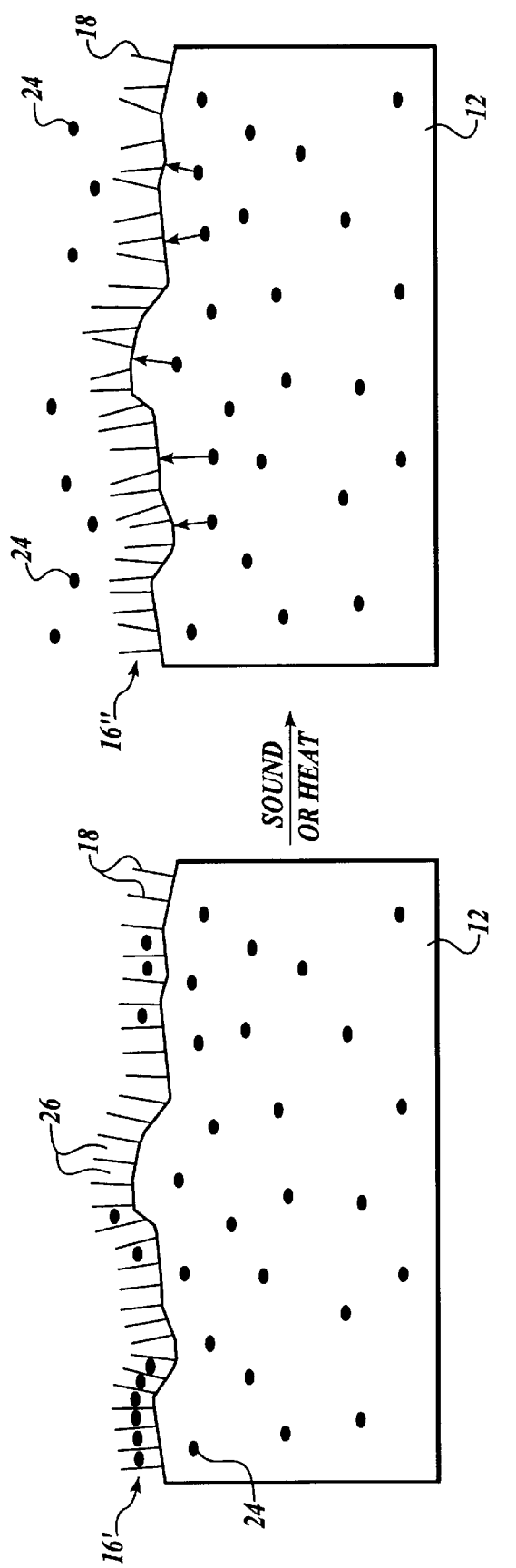
FIG. 3 shows an implantable drug delivery device of the invention that includes a surface layer that converts from an ordered state (capable of retaining drug molecules) to a less ordered state (that releases retained drug molecules) in response to an effective amount of sound or thermal energy.

Embodiments of biomedical device 10 that include drug molecules 24 disposed within substrate 12, and optionally also disposed in spaces 26 between molecules 18 of layer 16, are useful, for example, as implantable drug delivery devices. It is a feature of devices 10 of the invention that include drug molecules 24 disposed between molecules 18 of layer 16, that devices 10 release drug molecules 24 upon being subjected to an effective amount of sound or thermal energy. As exemplified in FIG. 3, embodiments of biomedical device 10 useful as implantable drug delivery devices possess surface layer 16 that has an ordered state 16' a less ordered state 16", less ordered state 16" being convertible from ordered state 16' in response to an effective amount of sound or thermal energy. Ordered state 16' of surface layer 16 is capable of retaining a multiplicity of drug molecules 18. Upon application of an effective amount of sound or thermal energy, surface layer 16 converts from ordered state 16' to less ordered state 16" and some, most or all drug molecules 24 are released from layer 16 because less ordered state 16" cannot retain them. Typically, the effective amount of sound or heat energy, in addition to causing the release of drug molecules 24 from surface layer 16, also stimulates the movement of drug molecules 24 from substrate 12 into layer 16. Thus, when an effective amount of sound or thermal energy is no longer applied to device 10, less ordered state 16" converts to ordered state 16' which traps drug molecules 24 (which have moved out of substrate 12 in response to sound or thermal energy) within spaces 26. Implanted device 10 is therefore ready to be used again to deliver drug molecules 24 to a subject.

In some embodiments of biomedical devices 10 adapted for use as implantable drug delivery devices, ordered state 16' of surface layer 16 forms a crystalline structure characterized by Fourier Infrared Peak Frequencies at $2850+/2$ $cm^{-1}$ and $2920+/-2cm^{-1}$. Typically, sound energy that is effective to stimulate the release of drug molecules 24 from layer 16 has a frequency of between 20 kHz and 100 kHz. Typically, sound energy is applied to device 10 for a period of from 2 minutes to 10 minutes, although the optimum time period (and sound frequency) can readily be determined by routine experimentation and will depend on a variety of factors including the type of material used to construct layer 16, and the size, shape and charge of drug molecules 24. Sound energy can be applied to device 10 as a series of pulses rather than as a single, continuous exposure. An effective amount of heat energy typically raises the temperature of layer 16 to between 10° C. and 50° C. In general, the longer the carbon backbone of alkyl molecules 18, the higher the temperature required to convert ordered state 16' to less ordered state 16", and so release drug molecules 24.

Figure 4C:
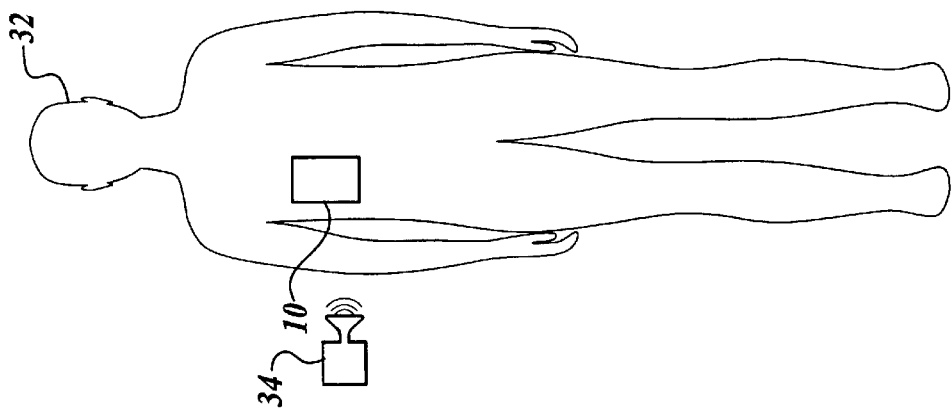
FIG. 4C shows a human body into which is implanted a drug delivery device of the invention, with a sound generator located external to the body.
Figure 4B:
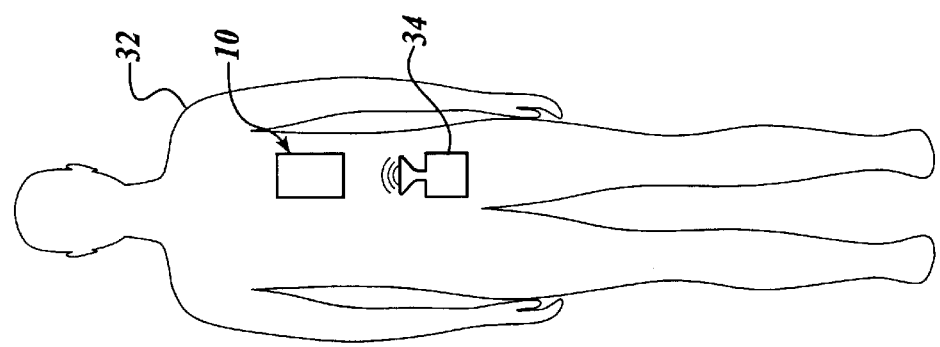
FIG. 4B shows a human body into which is implanted a drug delivery device of the invention and a separate sound generator.
Figure 4A:
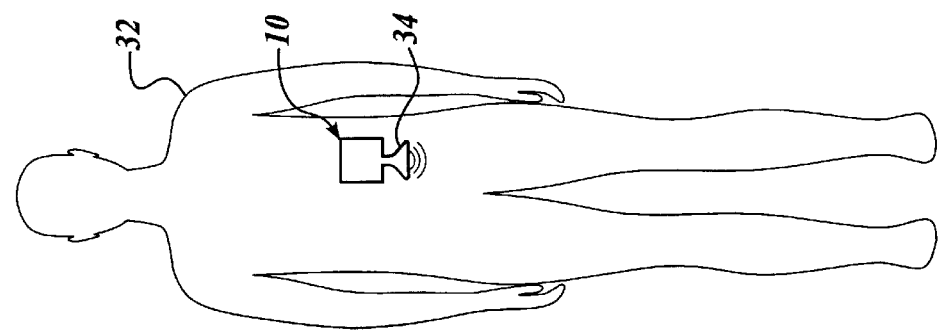
FIG. 4A shows a human body into which is implanted a drug delivery device of the invention which includes an integral sound generator.

Sound energy can be generated by a sound generator that is attached to device 10, or that is separate from device 10. For example, in those embodiments in which device 10 is an implantable medical device implanted into a subject's body, a sound generator can be utilized outside a subject's body, or can be attached to device 10 and implanted into the subject's body, or can be implanted into the subject's body separately from device 10. FIG. 4A shows a human body 32 into which is implanted a device 10 of the invention which includes an integral sound generator 34. FIG. 4B shows a human body 32 into which is implanted a device 10 of the invention and a separate sound generator 34. FIG. 4C shows a human body 32 into which is implanted a device 10 of the invention, while sound generator 34 is located external to body 32. Heat energy can be generated, for example, by application of a heating pad to a portion of a subject's skin close to the portion of the subject's body into which device 10 is implanted.

In some embodiments of the present invention in which device 10 includes insulin molecules 24 disposed within substrate 12, a sound generator 34 can be implanted into a subject's body, either attached to or separate from device 10. Sound generator 34 includes an insulin sensor that constantly or occasionally measures the level of insulin in the surrounding tissue or fluid and, if the measured level of insulin drops below a predetermined threshold level, sound generator 34 emits sound energy that causes the release of insulin 24 from device 10.

In those embodiments of device 10 that include effector molecules 30, depending on the choice of effector molecule 30, embodiments of device 10, such as the embodiment shown in FIG. 2B, can be adapted to reduce the foreign body reaction of the subject's body to implanted device 10 (for example, by utilizing effector molecules 30 that inhibit a component of the immune system that mediates the foreign body reaction), or can be adapted as an assay device wherein effector molecules 30 bind to a substance in a sample thereby facilitating the measurement of the amount of substance in the sample.

In another representative embodiment, device 10 can be adapted as a biosensor wherein effector molecules 30 bind to a substance in a sample thereby causing a response in device 10, such as a change in electrical current in device 10, thus facilitating detection of the substance in the sample (e.g., in a diagnostic assay). Such diagnostic applications include, but are not limited to, immunochemical detection of metabolites and protein markers for disease. Devices 10 of the present invention have several advantages for the immobilization of proteins and nucleic acids for application in medical diagnostic, genomic and proteomic analysis. These advantages include, but are not limited to, the use of hydrogels and other polymers to form polymeric substrate 12 at the surface of device 10 to improve functional density of the desired effector molecules 30. In the case of DNA or protein micro-arrays and sensors, a current limitation of existing technologies is the requirement for expensive surfaces, such as gold, to serve as the substrate. Devices 10 of the present invention provide a cheaper alternative.

The present invention also provides methods of making a drug delivery device, the methods comprising the steps of: (a) disposing a multiplicity of drug molecules within a polymeric or hydrogel substrate; and (b) covalently attaching a multiplicity of $C_{10}$ to $C_{22}$ unbranched alkyl molecules to the surface of the substrate by forming a covalent linkage between an end group on each member of the multiplicity of $C_{10\ to\ C22}$ unbranched alkyl molecules and a reactive group on the substrate, thereby forming a surface layer on the substrate wherein: (1) the multiplicity of alkyl molecules define a multiplicity of spaces therebetween; (2) each member of the multiplicity of alkyl molecules possesses a proximal end and a distal end, the proximal end being covalently linked to the substrate; and (3) the surface layer has an ordered state and a less ordered state, the surface layer being reversibly convertible to the less ordered state from the ordered state in response to an effective amount of sound or thermal energy. As described more fully in Examples 1 and 2, in one embodiment of the methods of this aspect of the invention, dodecyl ($C_{12}$) isocyanate molecules were reacted with surface hydroxyl functional groups on a cross-linked poly (2-hydroxyethyl methacrylate) (pHEMA) substrate 12 to form a predominantly all-trans, crystalline hydrophobic layer 16. The reaction was catalyzed by dibutyltin dilaurate. Allophanate side-branching reactions were not observed. Both X-ray photoelectron spectroscopy and time-of-flight secondary ion mass spectrometry showed that the surface reaction reached saturation after 30 min at 60° C. Unpolarized Fourier transform infrared-attenuated total reflection showed that, after 30 min, the stretching frequencies, $vCH_2$, asym and $vCH_2$,sym, decreased and approached 2920 and 2850 $cm^{-1}$, indicative of a crystalline phase. The distance between two hydroxyl groups was roughly 4 Å. A tilt angle of 33.5°+/−2.4° was estimated by dichroic ratios measured in polarized ATR according to the two-phase and Harrick thin film approximations.

Because of the presence of a hydroxyl group in the side chain of the polymer, various modifications of pHEMA using its primary alcohol are possible and provide a wide range of pHEMA derivatives useful for making substrates 12, and are described for example in Montheard, J-P., et al., *Homopolymers and Copolymers of 2-Hydroxyethyl Methacrylate for Biomedical Applications*; Reza, A., Ed., American Chemical Society: Washington D.C., 1997; ps. 699–711. A more complete overview of isocyanate chemistry (useful for attaching $C_{10}$ to $C_{22}$ unbranched alkyl molecules to a hydroxyl group on pHEMA or other polymer or hydrogel) is described in Arnold, R. G. et al., Chem. Rev. 1957, 57, 47–76, and in Saunders, J. H., et al., Chem. Rev. 1948, 43, 203–218.

Numerous polymers are useful for making substrate 12. Representative examples of synthetic polymers useful for making substrate 12 of implantable drug delivery devices include (poly)urethane, (poly)carbonate, (poly)ethylene, (poly)propylene, (poly)lactic acid, (poly)galactic acid, (poly)acrylamide, (poly)methyl methacrylate and (poly)styrene. Useful natural polymers include collagen, hyaluronic acid and elastin. Surface layer 16 can include $C_{10}$ to $C_{22}$ unbranched alkyl molecules that include halogen atoms (such as fluorine) in place of some or all of the hydrogen atoms attached to the carbon backbone.

Alkyl molecules 18 can be attached to substrate 12 by any suitable reaction. For example, the following pairs of reactive groups (each member of the pair being present on either substrate 12 or proximal end 20 of alkyl molecule 18) can be utilized to bond alkyl molecules 18 to substrate 12: hydroxyl/carboxylic acid to yield an ester linkage; hydroxyl/anhydride to yield an ester linkage; hydroxyl/isocyanate to yield a urethane linkage. Substrate 12 that does not possess useful reactive groups can be treated with radio-frequency discharge plasma etching to generate reactive groups (e.g., treatment with oxygen plasma to introduce oxygen-containing groups; treatment with propyl amino plasma to introduce amine groups).

While not wishing to be bound by theory, with respect to those embodiments of device 10 that include drug molecules 24 disposed within polymeric substrate 12, it is hypothesized that after hydrophobic layer 16 is formed on polymeric substrate 12, alkyl molecules 18 within layer 16 are aligned side-by-side with spaces 26 therebetween. Drug molecules 24 migrate, such as by diffusion, into spaces 26 between molecules 18 of layer 16. Thereafter, application of sound energy induces a transition in layer 16 from ordered state 16' to less ordered state 16" (e.g., by inducing cavitation within layer 16, thereby increasing the average distance between alkyl molecules 18 within layer 16) which permits release of drug 24. Upon cessation of sound energy, less ordered state 16" reverts rapidly to more ordered state 16' preventing further release of drugs 24. As exemplified in Example 3, when sound energy is no longer applied to device 10, typically the rate of release of drug 24 from layer 16 rapidly drops back to substantially (i.e., within 5%) the same rate of release of drug from layer 16 before application of sound energy (i.e., the rate of release of drug 24 drops back to approximately zero).

Thus, those embodiments of device 10 that include drug molecules 24 disposed within polymeric substrate 12 provide a means for repeatedly delivering desired amounts of drug 24 for a desired, discrete, time period to a subject in need thereof. The intensity and duration of sound energy required to deliver a desired dosage of a specific drug over a defined time period to a subject can be readily determined by routine experimentation.

In yet another aspect, the present invention also provides methods of delivering a drug to a subject, the method comprising the steps of: (a) introducing into a subject a device comprising: (1) a polymeric or hydrogel substrate comprising a multiplicity of drug molecules; and (2) a surface layer comprising a multiplicity of $C_{10}$ to $C_{22}$ unbranched alkyl molecules, wherein: (i) the multiplicity of alkyl molecules define a multiplicity of spaces therebetween; (ii) a multiplicity of drug molecules are disposed within said spaces; (iii) each member of the multiplicity of alkyl molecules possesses a proximal end and a distal end, the proximal end being covalently linked to the substrate; and (iv) the surface layer has an ordered state and a less ordered state, the surface layer being reversibly convertible to the less ordered state from the ordered state in response to an effective amount of sound or thermal energy; and (b) subjecting the device to an amount of sound or thermal energy effective to induce release of the drug molecules from the surface layer.

Implantable medical devices of the invention are useful in the methods of this aspect of the invention. Any drug that can be sequestered between alkyl molecules 18 of layer 16 can be utilized in this aspect of the invention. By way of representative example, proteins, peptides, nucleic acids, insulin, estrogens, androgens, cancer chemotherapeutics, hypnotics, anti-psychotics, narcotics, diuretics and other blood-pressure-regulating drugs can be utilized in this aspect of the invention. The duration and intensity of the pulse of sound energy required to release drug from layer 16 will depend on such variables as the size, shape and charge of the drug, and can be readily determined by routine experimentation (e.g., by immersing several identical devices 10 in a solution that simulates the chemical composition of mammalian tissue, and subjecting each device 10 to a different intensity and/or duration of sound energy and then measuring the amount of drug released into the solution). More than one type of drug can be included within device 10, and selective release of one or all types of drug can be achieved by applying sound energy having an intensity and duration that preferentially causes release of the desired drug or drugs.

The following examples merely illustrate the best mode now contemplated for practicing the invention, but should not be construed to limit the invention. All literature citations herein are expressly incorporated by reference.

EXAMPLE 1

This example describes the materials and methods used to make devices 10 utilized in the experiments described in the subsequent examples.

Materials and Methods:

2-Hydroxyethyl methacrylate (HEMA, no. 04675) monomer with a purity of more than 99.5% and tetraethylene glycol dimethacrylate (TEGDMA, no. 02654) were purchased from Polysciences Inc., Warrington, Pa. Ethylene glycol (no. 32,455-8), sodium metabisulfite (no. 16,151-9), ammonium persulfate (no. 24,861-4), anhydrous tetrahydrofuran (THF, no. 40,175-7), dodecyl isocyanate ($C_2$ isocyanate, no. 29,123-4), and dibutyltin dilaurate (no. 38,906-4) were received from Aldrich, Inc. All chemicals were used as received. Glass plates and glass apparatus for synthesis were soaked in 2% RBS-35 detergent (no. 27950, Pierce) overnight and rinsed with Millipore purified water prior to the experiments.

Preparation of Polymeric Substrate 12

Cross-linked hydrogel slabs were synthesized from HEMA. Briefly 0.5 g of HEMA monomer and 0.2 g of the TEGDMA cross-linking agent were added to a water/ethylene glycol mixed solvent (1 g/1.5 g with 1 mL of 15%sodium metabisulfite and 40% ammonium persulfate as redox initiators to begin the radical polymerization. The mixture was allowed to polymerize between two clean glass plates with a Teflon gasket of thickness 0.025 in. Although the gel set within an hour, the film was allowed to stand overnight. The pHEMA film was released from the glass plates and soaked in distilled water for a few days to leach out unreacted monomers, initiators, and oligomer residues. To speed the leaching process, later films were soaked in water for only 1day. After leaching, the pHEMA film was cut into smaller specimens for surface modification with $C_{12}$ isocyanate. The pHEMA samples must be vacuum-dried prior to surface derivatization because water molecules easily terminate the urethane-linkage reaction between the hydroxyl group on the pHEMA surface and the isocyanate on the $C_{12}$ compound.

Preparation of Layer 16 on pHEMA Substrate 12

In a three-necked round-bottom flask connected to a nitrogen gas line, 4.5 mL of $C_{12}$ isocyanate (5%) and 0.18 mL of dibutyltin dilaurate (as the catalyst, 0.3%) were added to 90 mL of anhydrous tetrahydrofuran containing the dry polymer films. In this case, the choice of the reaction medium is important. Tetrahydrofuran is a poor swelling solvent for pHEMA which prevents polymer swelling and optimizes the surface immobilization reaction of hydrocarbon chains to the gel slab. To further optimize the reaction conditions, temperature and reaction time were studied. The reaction was performed under a nitrogen atmosphere at 40, 50, or 60° C. in an oil bath. At each temperature, the reaction was allowed to run for 5, 15, 30, 45, and 60 min. At each time point, one pHEMA sample was retrieved from the reaction flask and sonicated (43 kHz, L&R model T21) in fresh THF for 5 min to remove physically adsorbed $C_{12}$ isocyanate. Following sonication, the surface-derivatized films were blown dry with nitrogen for surface characterization.

Surface Characterization of Device 10

Devices 10 were examined by a number of surface characterization techniques. XPS was used to measure the chemical composition and functional groups of layer 16. TOF-SIMS to study the molecular fragments that were chemically bonded to substrate surface 14. FTIR-ATR to investigate the chain order and crystalline structure, and polarized ATR to estimate the molecular chain orientation of layer 16.

X-ray Photoelectron Spectroscopy.

XPS, also known as electron spectroscopy for chemical analysis (ESCA), was performed with an S-Probe surface analysis system (Surface Science Instruments, Mountain View, Calif.) using a monochromatic Al K$_{1,2}$ X-ray source to stimulate photoemission. The system consists of a 30° solid angle acceptance lens, a hemispherical analyzer, and a position-sensitive detector. All polymer samples were analyzed at a 55° takeoff angle, probing the uppermost 50–80 Å of the surface. The takeoff angle was defined as the angle between the surface normal and the axis of the analyzer acceptance lens. Survey scans (0–1000-eV binding energy) were run at an analyzer pass energy of 150 eV (resolution 4) with an X-ray spot size of 1000–1700 μm to determine the elemental composition of each surface. High-resolution O (1s), C (1s), and N (1s) scans were obtained at a pass energy of 50 eV (resolution 2). The high-resolution spectra were resolved into individual Gaussian peaks using a least-squares fitting routine in the SSI software. The chemical composition of each surface was determined from the peaks resolved in the high-resolution scans. All binding energies (BEs) were referenced by setting the maximum of the resolved C (1s) peak, corresponding to carbon in a hydrocarbon environment (CHx), to 285.0 eV. When the binding energy referencing was performed in the same manner, the primary O (1s) peak was found to be shifted to 532.8 eV, the expected value for oxygen in an ether environment in polymers. A 5-eV electron flood gun was used to minimize surface charging. Typical pressures in the analysis chamber during spectral acquisition were $10^{-9}$ Torr. XPS analysis was carried out on devices 10 immediately after layer 16 was formed on substrate 12, unless otherwise specified.

Time-of-Flight Secondary Ion Mass Spectroscopy

TOF-SIMS was performed on a model 7200 Physical Electronics PHI instrument (Eden Prairie, Minn.). An 8-keV Cs+ ion source was used for surface impingement, a low-energy pulsed electron flood gun for charge neutralization and a chevron-type multichannel plate (MCP) for secondary ion detection. Data were acquired over a mass range from m/z 0–1000 for both positive and negative secondary ions. The mass scale for the negative secondary ions was calibrated using peaks originating from HOCH=CHO$^-$(m/z 59$^-$), CH$_3$C(CH$_2$)CHOO$^-$ (m/z85$^-$) and C$_{13}$H$_{26}$NO2$^-$ (m/z 288$^-$). The first two were fingerprints originating from pHEMA substrate 12 while the third one resulted from the C$_{12}$-urethane fragment of layer 16. Both spectroscopic and imaging modes were employed. Images and spectra were analyzed with TOF-Pak software packages provided by Physical Electronics.

Fourier Transform Infrared Spectroscopy-Polarized Attenuated Total Reflection Mode.

FTIR-ATR measurements were performed in the mid-IR frequency range (4000–400 cm$^{-1}$) on a Digilab FTS-60A spectrometer equipped with a liquid nitrogen-cooled mercury-cadmium-telluride detector. The system was purged with water and carbon dioxide free air. An internal reflection cell with a variable-angle holder (model 300, SpectraTech CT) was used to measure FTIR-ATR spectra. The incidence angle for internal reflection was calculated using the procedure described in the model 300 manual and was set to 45°. Either unpolarized or s- and p-polarized light was used. For polarized spectra, the KRS-5 grid polarizer (SpectraTech) was set to 0° and 90°, giving absorbance perpendicular (s) and parallel (p) to the plane of incidence, respectively. The IR beam was aligned and calibrated prior to measurements. The background spectrum for all ATR measurements was the single-beam spectrum of the clean KRS-5 element (parallelogram, 50×10×3 mm, 45°) and the absorbance spectra of the modified films were taken as a ratio against the background spectrum of a clean KRS-5 element. All data were taken at 4 cm$^{-1}$ resolution with a total of 64 scans to achieve adequate signal/noise. Spectra were baseline-corrected, and both asymmetric (2850 cm$^{-1}$) and symmetric (2920 cm$^{-1}$)CH$_2$ stretching frequencies were normalized against internal C=O (aliphatic ester at 1720 cm$^{-1}$) to obtain the polarized dichroic ratio (i.e. $A_p$ $A_s$). The ratio was later used to calculate the molecular orientation of methylene chains using the two-phase approximation and the Harrick thin film approximation.

EXAMPLE 2

This example describes the preparation and characterization of a dodecyl isocyanate surface layer 16 formed on a pHEMA substrate 12. Characterization of a dodecyl isocyanate layer 16 formed on a pHEMA substrate 12

Briefly, the available hydroxyl groups on the pHEMA were, in a concerted fashion, catalyzed to form urethane bonds with the available isocyanate groups on dodecyl isocyanate as these alkyl molecules self-assembled on the surface of the hydrogel to form surface layer 16.

XPS and TOF-SIMS Analysis

A typical C (1s) XPS Spectra (not shown) of C$_{12}$ surface layer 16 on pHEMA substrate 12 with different reaction times at 60° C. showed an increase of the CH$_x$ (methylene) and the disappearance of C—OH/CO peaks which is indicative that hydroxyl groups in pHEMA are reacting with the isocyanate. Further evidence for the desired reaction was the broadening of the O—C=O peak (compared to the control reaction containing C$_{12}$ isocyanate but no catalyst), presumably due to its conversion into the urethane bond.

A typical O (1s) XPS Spectra (not shown) of C$_2$ surface layer 16 on pHEMA substrate 12 from the samples described in the preceding paragraph showed that the broad, but symmetrical, O (1s) peak observed in pHEMA is split into two peaks represented by the two types of oxygen present in the urethane bond. Confirmation for this reaction was also obtained via derivatization of pHEMA with trifluoroacetic anhydride (TFAA, data not shown).

Normalized peak intensities of various representative negative molecular ions (via TOF-SIMS) originating from pHEMA during various reaction times showed that the major moieties from pHEMA disappear during the reaction within 30 min . This is consistent with XPS analysis (data not shown). Total ion intensity was calculated as the sum of the intensities of all relevant ion species specific to pHEMA and the derivatized surface layer 16. No detection of a peak characteristic of allophanate (m/z=4393899476) was observed. Uncoated pHEMA substrate 12 was used as a control for comparison.

The relative normalized peak intensities of various representative negative molecular ions originating from surface layer 16 during various reaction times was determined via TOF-SIMS. The data showed that the major moieties (mostly nitrogen-containing) of the derivatized surface layer 16 appeared during the reaction within 30 min . This was also confirmed by XPS analysis (data not shown). Total ion intensity was determined as described in the preceding paragraph. Furthermore, TOF-SIMS imaging for the C$_{12}$-urethane fragment demonstrated a uniform formation of the C$_{12}$ surface layer 16 compared to no detection of this fragment on uncoated pHEMA substrate 12. Finally, using the peak area of the C$_{12}$ urethane negative ion (m/z=228$^-$) as a fraction of total contribution of pHEMA (sum of area of peaks with m/z=59$^-$ and 85$^-$, it was confirmed that the reaction is complete within 30 minutes. Uncoated pHEMA substrate 12 was used as a control for comparison.

Unpolarized FTIR-ATR

The unpolarized IR spectra (not shown) of dry, pHEMA substrate 12 bearing C$_{12}$ layer 16 at different reaction times, consistent with the conclusion from SIMS, showed that characteristic IR bands for allophanate were not observed. Allophanates are normally characterized by a triplet of intense bands at 1220, 1280, and 1310 cm$^{-1}$ associated with the skeletal vibrations of the allophanate group as well as unique NH bands at 3298, 3267, and 3233 cm$^{-1}$. The absence of these bands in the IR spectra demonstrated that undesirable allophanate formation had not occurred. Furthermore, the absence of the NCO band at 2270 cm$^{-1}$ suggested that free isocyanates were not physisorbed to the surface after the 5-min sonication.

The absorbance of the CNH stretching peak at 1530 cm$^{-1}$, due to the secondary urethane, increased with increasing reaction time and so did the methylene scissoring vibration frequency (1453 cm$^{-1}$). Two carbonyl stretching frequencies in the range 1705–1750 cm$^{-1}$ showed a reversal of intensities: the IR absorbance of the aliphatic ester (O—C=O; 1720 cm$^{-1}$) from pHEMA substrate 12 decreased and that of secondary urethane amide (1705 cm$^{-1}$) from C$_{12}$-layer 16 increased with increasing reaction time. Third, the strong, broad OH band at 3300 cm$^{-1}$ also narrowed and exhibited similarity to an NH stretching peak. All lines of evidence suggested that a successful attachment of C$_{12}$ methylene chains via covalent urethane bonding was achieved. Another important observation is associated with the frequency change of the CH$_2$ stretching frequencies 2850–2920 cm$^{-1}$. The frequencies of the $\nu$ CH$_{2,asym}$ and $\nu$ CH$_{2,sym}$ bands decreased and approached 2920 and 2850 cm$^{-1}$ with increased amplitudes at longer reaction times (0–30 min ).

After a 30-min reaction time, both the ν $CH_{2,asym}$ and ν $CH_{2,sym}$ stretching frequencies were found to be stabilized at 2920 and 2851 cm$^{-1}$, typical peak frequencies of $CH_2$ units in the trans state, indicating the immobilized methylene chains in surface layer 12 ordered themselves in a crystalline structure. The increased amplitudes of the $CH_2$ IR peaks along with other observations consistently pointed to increased surface coverage at longer reaction times.

Polarized FTIR-ATR s-Polarized and p-polarized ATR spectra (not shown) of a dry, 30-min-pHEMA substrate 12 bearing a $C_{12}$ layer 16 on a KRS-5 element showed that $CH_{2,asym}$ and $CH_{2,sym}$ frequencies at 2920 and 2850 cm$^{-1}$ are easily distinguished in the spectra. To determine the orientation of the axis of the methylene chain 18 with respect to the normal to the ATR crystal, that is, the tilt angle (θ), the dichroic ratio ($A_p/A_s$ can be calculated from the polarized spectra according to linear dichroism theory where $A_p$ and $A_s$ are the absorbances of the bands obtained with infrared radiation polarized parallel and perpendicular to the plane of incidence, respectively. Because absorbance strongly depends on the pressure with which the sample is flattened to the ATR crystal and it may vary from experiment to experiment, the aliphatic ester (O—C=O) stretching frequency at 1720 cm$^{-1}$ was chosen as the internal reference and used to normalize the observed absorbances of all $CH_2$ stretching frequencies. The calculated dichroic ratios for $CH_{2,asym}$ (2920 cm$^{-1}$) and $CH_{2,sym}$ (2850 cm$^{-1}$) are 1.004 and 0.967, respectively.

Using both the two-phase and the Harrick thin film approximations. The tilt angles calculated in both cases ranged from 30° to 36°. The tilt angles calculated with two ν $CH_{2,asym}$ and ν $CH_{2,sym}$ stretching frequencies differed by only 1°, indicating either peak intensity could be used in estimating the tilt angle without significant errors. Furthermore, it appears that both theories gave similar average tilt angles except when the refractive index of $C_{12}$-urethane=1.4 was used. The tilt angles increased from 30° to 34° for n2=1.4 at 2850 cm−1 and from 31° to 35° for n2=1.5 at 2920 cm−1 in the Harrick thin film approximation. In fact, for tilt angles<30°, the discrepancy in the tilt angle for refractive indices between 1.4 and 1.5 is approximately the same as that due to the experimental error in the determination of the dichroic ratio. In addition to the uncertainty about the values of the refractive index, other factors also may affect the accuracy of orientation measurements, such as the exact thickness of the thin film, the presence of surface irregularities on the ATR element, conformational disorder along the methylene chains, and the assumption of uniaxial configuration. In summary, the average tilt angle found by both approximations was 33.5°+/−2.4°.

The evidence for the nature of the $C_{12}$ coverage on substrate 12 is supported by corroborative data from a number of techniques. As mentioned earlier, XPS has been shown to generate accurate stoichiometric data for organic polymers. The C/O ratio for a pHEMA film is expected to be 2.0. Experimentally, values of ≈2.3 were obtained here. Pure dodecyl isocyanate would have a C/O ratio of 13. A derivatized monomer unit consisting of one pHEMA monomer unit+one dodecyl isocyanate unit has a C/O ratio of 4.75. C/O values close to 5 were obtained for the 60° C., 30-min reaction time over an XPS sampling depth of 50–80 Å. This is consistent with stoichiometric reaction over the entire surface layer 16. The precise thickness of layer 16 cannot be determined from these data, but it is thicker than the XPS sampling depth. If $C_{12}$ layer 16 was only a layer (roughly 20-Å thick), one would expect to see a C/O value between 4.75 and 2.0 (20 Å of layer 16 on top of 60 Å of pHEMA substrate 12). The SIMS data support the idea of stoichiometric reaction within a surface zone in that, at plateau levels of reaction measured by XPS (>30 min), substantial m/z 59—peak intensity is still seen. The IR data point to considerable crystallinity and orientation within the hydrocarbon chains. However, the ATR sampling depth is 1–5 μm. The fact that, at 30 min, the ATR signals associated with the hydrocarbon chains are intense suggests the reacted zone may be microns thick. If a slab of device 10 is cut in half, a clear zone is seen in the center of the material, surrounded by a translucent "halo." On the basis of all data, a structural model is proposed. A surface zone, the thickness of which is governed by reaction time, consists of stoichiometrically reacted $C_{12}$ chains. The chains are sufficiently close to each other to permit crystallization or organization, as has been observed in several polymers with long alkyl side chains.

The tilt angle of ≈30° noted here is associated with the most efficient packing of the zigzag, all-trans methylene molecules 18 to maximize van der Waal interactions. To further support the model that layer 16, prepared in accordance with Examples 1 and 2 herein, has ordered structural organization, the surface density of the hydroxyl groups available on pHEMA surface 14 can be approximated. This was done by using the XPS composition data from the TFAA (trifluoroacetic anhydride) derivatization experiment described earlier. For complete stoichiometric reaction of one pHEMA monomer unit+one TFAA, a theoretical composition of 20.0%, 53.3%, and 26.6% fluorine, carbon, and oxygen, respectively, is expected. In the XPS survey scan, experimental values of 20.4% fluorine, 54.0% carbon, and 25.6% oxygen were obtained, indicating a complete surface reaction. Because three fluorine atoms are associated with each —OH, the density of the reactive hydroxyl groups on the original pHEMA was then back-calculated by dividing the experimental fluorine percentage by a factor of 3, yielding a hydroxyl group composition of 6.81%. Furthermore, on the basis of the density (1.073 g/cm 3) and molecular weight (130.1 g/mol) of HEMA along with the analyzed volume (1000×1700-μm, 50–80-Å deep) in the XPS at a takeoff angle of 55°, it was estimated that there is 0.25 hydroxyl molecule per Å$^2$. Assuming the hydroxyl groups are distributed evenly, then there is ≈1 hydroxyl group per every 4 Å. This spatial distance agrees well with the effective packing of alkyl chains at the ≈30° tilt angle. In addition, the area per molecule of long, close-packed alkyl chain thiols on Au(111) is reported to be 21.7 Å$^2$ (square root=4.7 Å). Because our hydroxyl spacing is roughly 4 Å and our calculated average tilt angle is ≈33.5°, we believe that we have established a closed-packed, multilevel all-trans structure, within surface 14.

EXAMPLE 3

This example shows the controlled release of drugs from a device 10 of the present invention.

Figure 5:
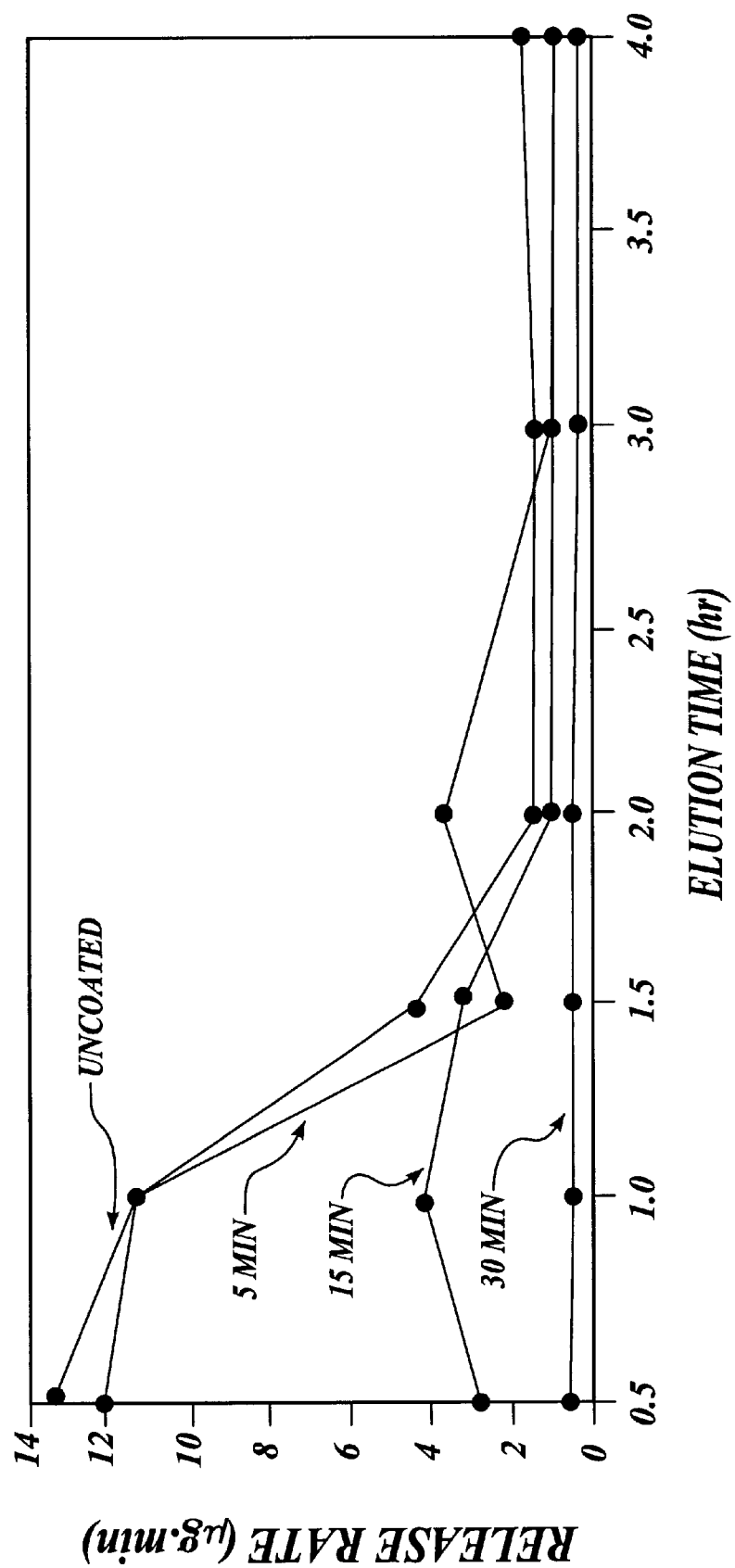
FIG. 5 shows release of ciprofloxacin (in the absence of ultrasound irradiation) from drug delivery devices of the invention. The drug delivery devices had been coated with $C_{12}$ methylene chains for periods of 5, 15 and 30 minutes. A pHEMA substrate without a $C_{12}$ layer was used as the control. Release rate is micrograms per minute ($\mu$g/min).

$C_{12}$-methylene chains were coated onto ciprofloxacin-containing pHEMA for various times (5, 15 & 30 min). Initially, it was important to assess the release of ciprofloxacin from the $C_{12}$-coated pHEMA in the absence of ultrasound. The data depicted in FIG. 5 demonstrate that, when placed in an aqueous environment, $C_{12}$-layer 16 has a much lower release rate into the medium, compared to that observed for the uncoated pHEMA control. Furthermore, the initial burst release of the antibiotic was eliminated by $C_{12}$-layer 16. As suggested from the XPS and TOF-SIMS analysis, the progress of the reaction was also confirmed in this experiment. There is little difference in the release of ciprofloxacin in the material from a 5 min. reaction vs. the uncoated pHEMA, while complete control of antibiotic release is apparent after 30 min. of reaction time.

Figure 6:
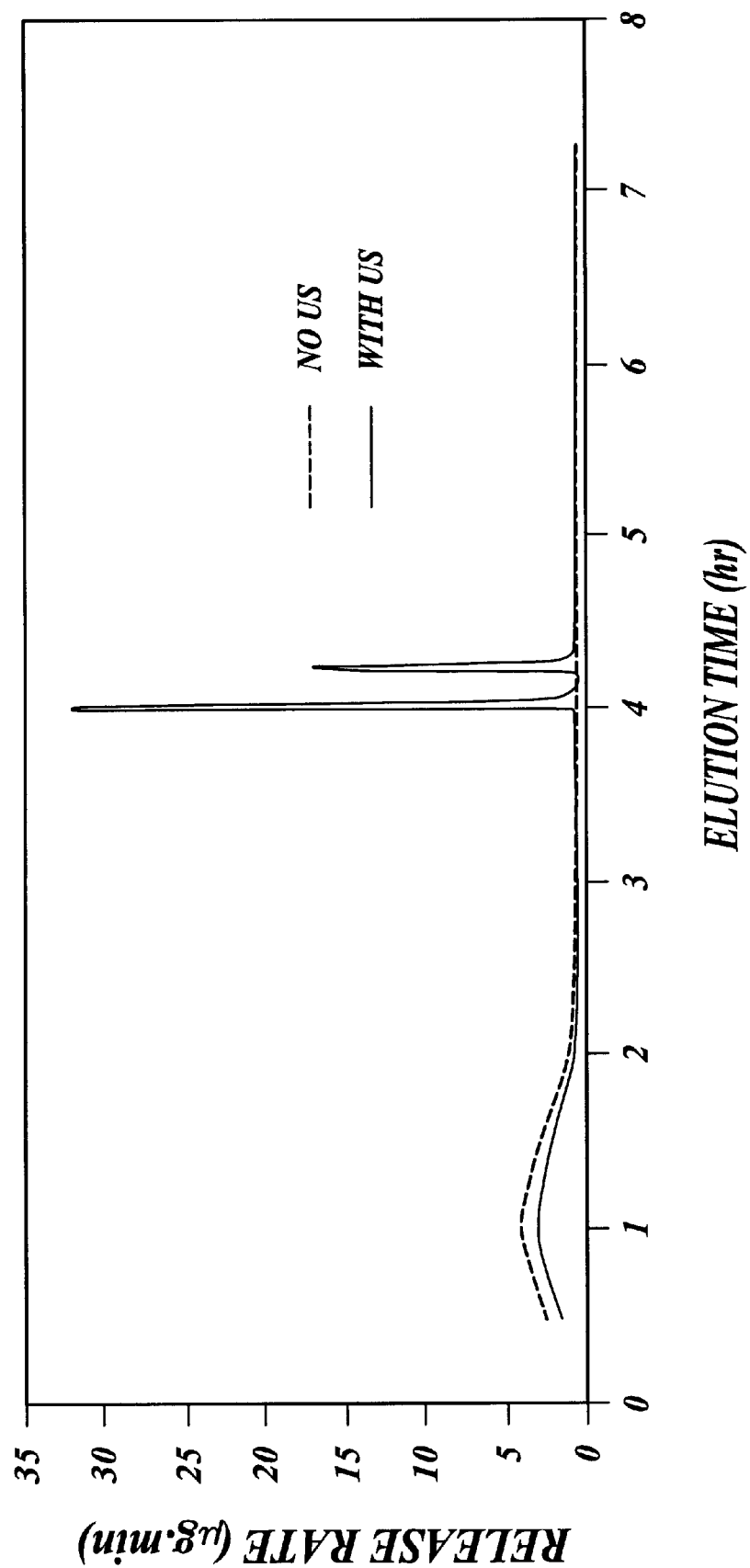
FIG. 6 shows release of ciprofloxacin from a drug delivery device of the invention, made from a pHEMA substrate coated with a $C_{12}$ layer, in the presence (with US) or absence (no US) of ultrasound irradiation. Release rate is micrograms per minute ($\mu$g/min).

FIG. 6 depicts the result of applying ultrasound (1.1 MHz at PRF 1 Hz and 10 ms pulse width) to device 10 comprising pHEMA substrate 12 coated with $C_{12}$ layer 16, compared to an identical device 10 without ultrasound. The effect of two consecutive pulses clearly demonstrates the release of drug in a pulsatile manner. The effect of the ultrasound was to reverse, temporarily, the restraint imposed on the drug release from $C_{12}$ layer 16. Most important is the fact that the release of the antibiotic returns to baseline after the ultrasound is turned off. This clearly demonstrates the reversibility of drug release from $C_{12}$ layer 16, and indicates its high potential for controlled drug release. These results indicate that the $C_{12}$ layer 16 reassembles between ultrasound pulses.

Figure 7:
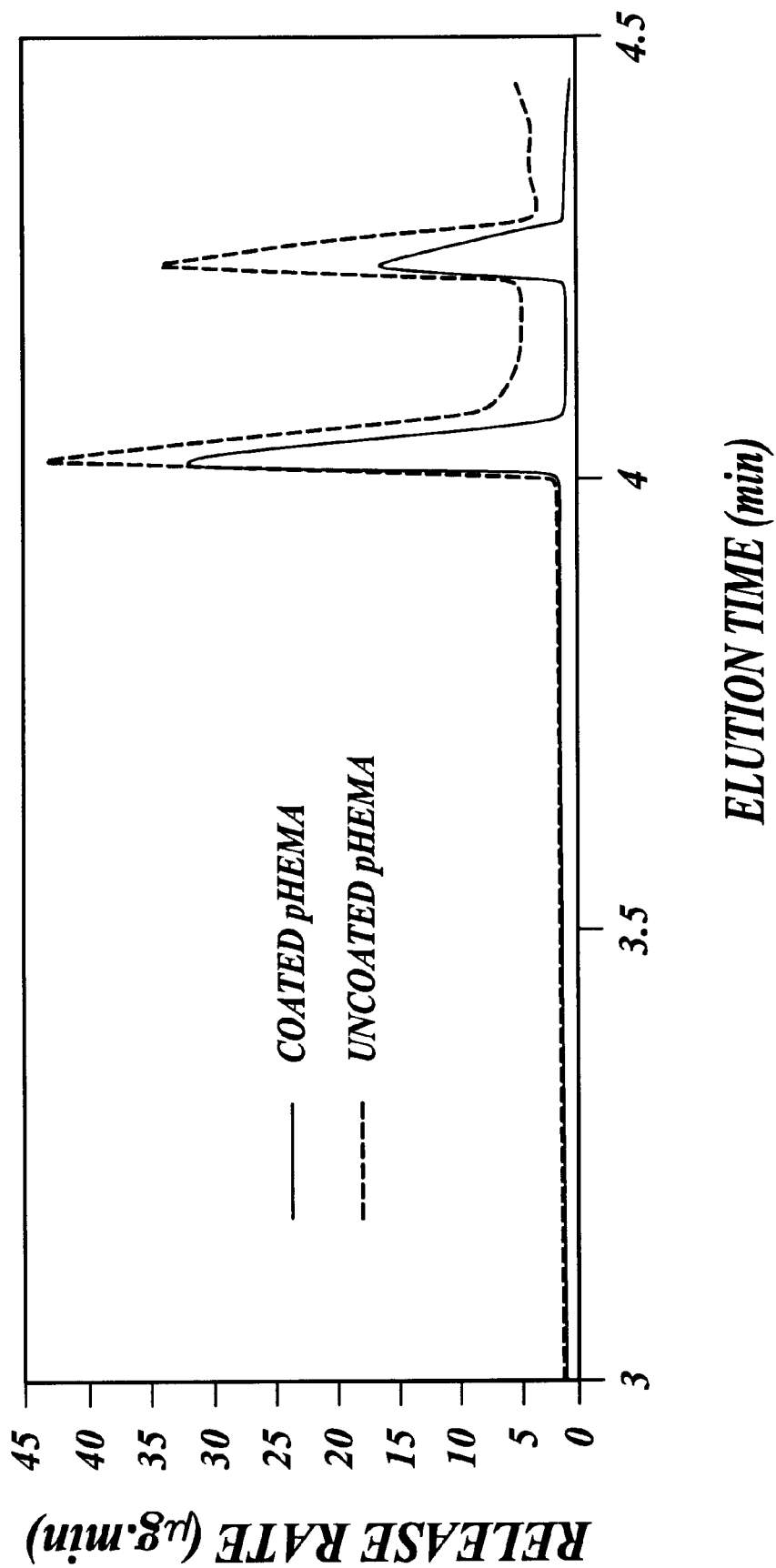
FIG. 7 shows the effect of ultrasound on release of ciprofloxacin from ciprofloxacin-loaded pHEMA substrate (uncoated pHEMA) and pHEMA substrate coated with a $C_{12}$ layer (coated pHEMA). Release rate is micrograms per minute ($\mu$g/min).

It was important to study the effect of ultrasound on the reservoir of ciprofloxacin in pHEMA substrate 12 itself, without $C_{12}$ layer 16 being present. FIG. 7 depicts the comparison of applying ultrasound to ciprofloxacin loaded pHEMA substrate 12 and pHEMA substrate 12 coated with $C_{12}$ layer 16. Ultrasound disturbs pHEMA substrate 12 antibiotic reservoir and causes a similar pulsatile release of the drug as compared to pHEMA substrate 12 coated with a $C_{12}$ layer 16. However, the baseline observed between the two ultrasound pulses does not return to the negligible release observed for pHEMA substrate 12 coated with $C_{12}$ layer 16. Further evidence of the control exerted by $C_{12}$ layer 16 is observed with the significantly higher release of the drug from the uncoated pHEMA substrate 12.

Figure 8:
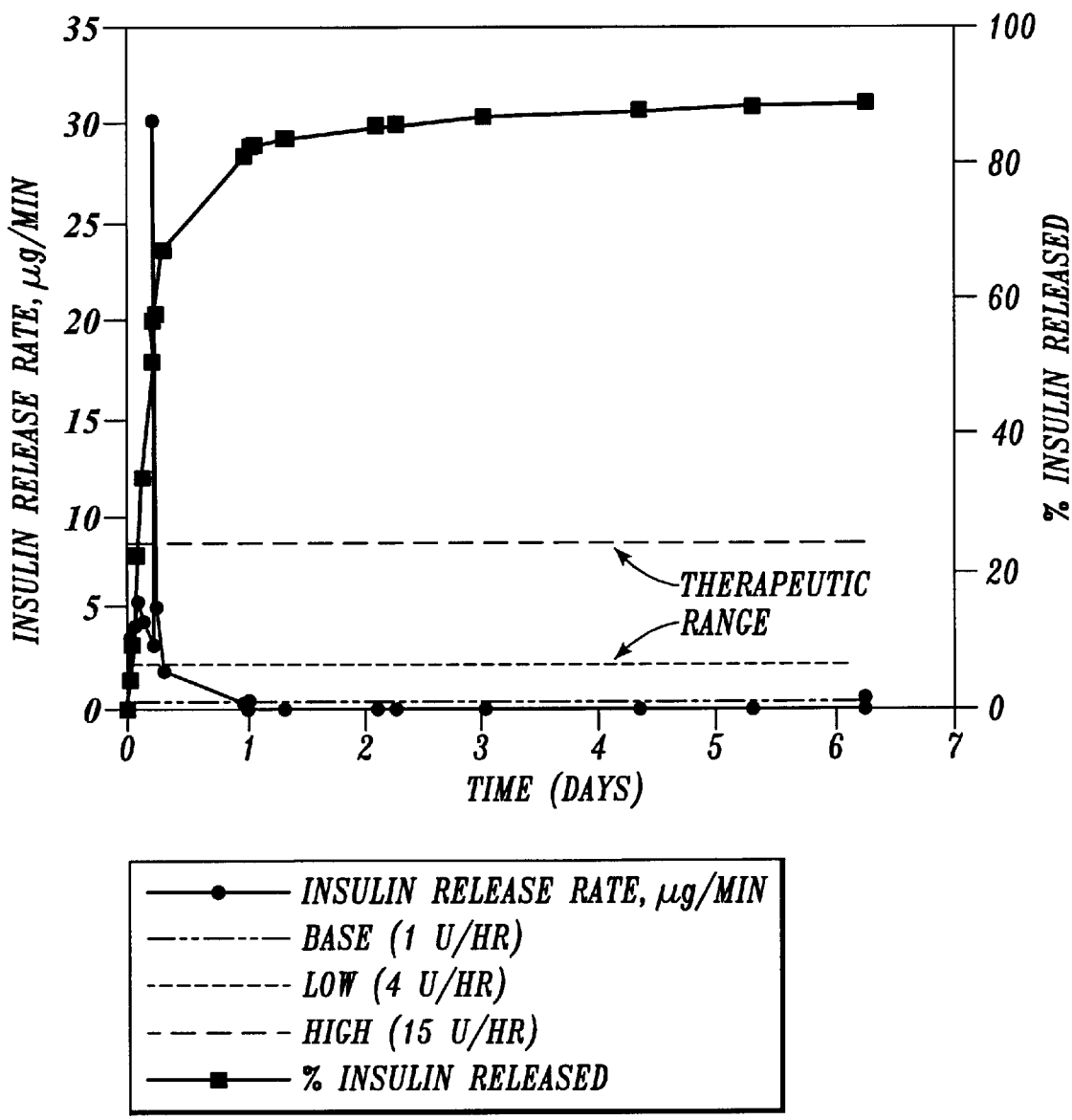
FIG. 8 shows the effect of ultrasound on delivery of insulin from a drug delivery device that included a pHEMA substrate, but which was not coated with an effective surface layer. The pHEMA was reacted for 5 minutes with $C_{12}$ isocyanate (insufficient time to form an effective $C_{12}$ barrier). Ultrasound was applied to the device at the time points indicated by shaded circles in FIG. 8. Sound energy was applied as a 40 KHz continuous wave for 5 minutes at an average intensity of 0.28 W/cm$^2$.
Figure 9:
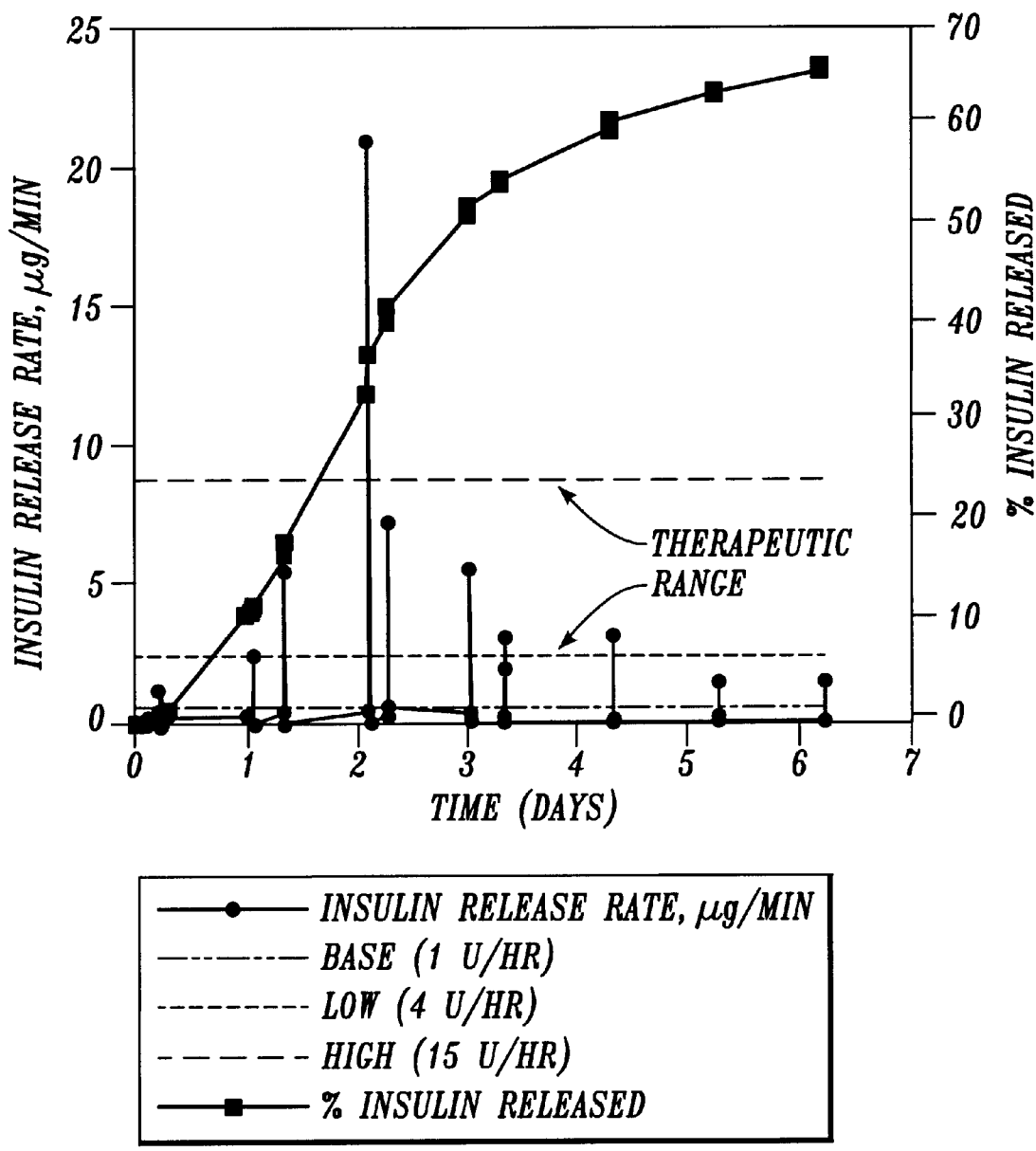
FIG. 9 shows the effect of ultrasound on delivery of insulin from a drug delivery device of the invention that included a pHEMA substrate coated with an effective surface $C_{12}$ layer. The pHEMA was reacted for 15 minutes with $C_{12}$ isocyanate to form the $C_{12}$ surface layer. The insulin-containing device was subjected to two five minute pulses of ultrasound, at each data point. (40 KHz continuous wave at average intensity of 0.28 W/cm$^2$.

To assess the capabilities of pHEMA substrate 12 coated with $C_{12}$ layer 16 in the delivery of peptide drugs, the control of insulin release by application of ultrasound (1.1 MHz, 300 mV)) to vacuum dried pHEMA substrate 12 containing insulin (2–3 mg insulin per 9.4 mm diameter disk with 0.64 mm pHEMA substrate 16 thickness) was studied. FIGS. 8 and 9 display a comparison of pHEMA substrate 12 coated with $C_{12}$ isocyanate for 15 minutes (FIG. 9) with samples reacted for only 5 minutes (FIG. 8) with the $C_{12}$ isocyanate in the presence of catalyst. As shown in FIG. 8, a reaction time of 5 minutes with the $C_{12}$ isocyanate was insufficient to form surface layer 16 effective to retain a substantial proportion of insulin 24 within substrate 12 after only a few exposures to ultrasound (i.e., drug delivery device 10 was rapidly depleted of insulin). The burst release of insulin (without ultrasound) was also eliminated in the pHEMA substrate 12 coated with a $C_{12}$ layer 16 compared to the pHEMA substrate 12 without effective layer 16.

By comparison, insulin-containing, pHEMA substrate 12 coated with an effective $C_{12}$ surface layer 16 (FIG. 9) was capable of delivering amounts of insulin within a desired therapeutic range (4–15 units/hr) for more than 2 days when pulsed for 2–5 minutes with ultrasound. Furthermore, the delivery of insulin in amounts greater than plasma baseline levels (1 unit/hr) was still possible after 4 days. The initial "burst" rate of insulin release, characteristically high without an effective surface layer 16, was also absent in the first few hours in pHEMA substrate 12 coated with $C_{12}$ layer 16 (FIG. 9).

Figure 10:
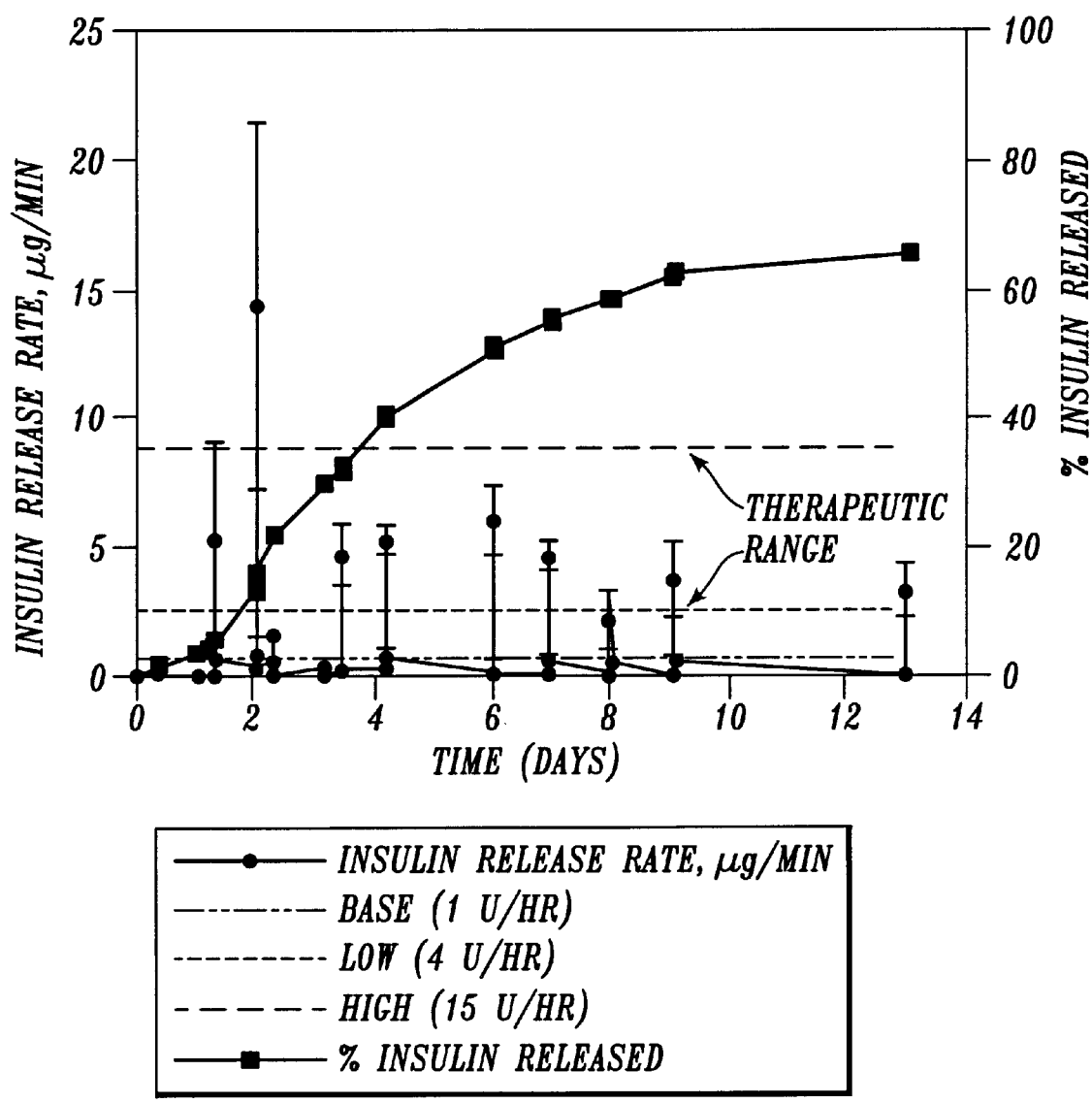
FIG. 10 shows the effect of ultrasound on the release of insulin from a drug delivery device of the invention made from a pHEMA substrate coated with a $C_{18}$ surface layer. The insulin release rate (filled circles) was measured immediately before and after application of ultrasound. Open circles represent percentage of insulin released.

FIG. 10 shows that a drug delivery device 10 of the invention coated with a $C_{18}$ surface layer 16 permits controlled release of insulin 24 over a longer time period (at least 6 days) than a comparable drug delivery device 10 of the invention coated with a $C_{12}$ surface layer 16 (see FIG. 9).

Insulin released from drug delivery devices 10 of the invention retains its biological activity as assessed by measurement of the ability of released insulin to regulate 14C-deoxyglucose uptake by culture 3T3-L1 adipocyte cells.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A biomedical device comprising:
   (a) a polymeric or hydrogel substrate; and
   (b) a surface layer comprising a multiplicity of $C_{10}$ to $C_{22}$ unbranched alkyl molecules, wherein:
      (1) the multiplicity of alkyl molecules define a multiplicity of spaces therebetween;
      (2) each member of the multiplicity of alkyl molecules possesses a proximal end and a distal end, the proximal end being covalently linked to the substrate; and
      (3) the surface layer has an ordered state and a less ordered state, the surface layer being reversibly convertible to the less ordered state from the ordered state in response to an effective amount of sound or thermal energy.

2. The biomedical device of claim 1, wherein the device is capable of retaining a multiplicity of drug molecules within the multiplicity of spaces when the surface layer is in the ordered state, and wherein the surface layer releases at least some of the retained drug molecules when the surface layer is converted from the ordered state to the less ordered state in response to an effective amount of sound or thermal energy.

3. The device of claim 1, wherein the surface layer consists essentially of a multiplicity of $C_{10}$ to $C_{22}$ unbranched alkyl molecules, each of the $C_{10}$ to $C_{22}$ alkyl molecules being covalently attached to the substrate.

4. The device of claim 3, wherein the length of the unbranched alkyl molecules is from $C_{12}$ to $C_{18}$.

5. The device of claim 1, wherein the substrate consists essentially of poly (2-hydroxyethyl methacrylate), and the surface layer consists essentially of $C_{12}$ to $C_{18}$ unbranched alkyl molecules.

6. The device of claim 1 further comprising a multiplicity of drug molecules disposed in a location selected from the group of locations consisting of:
   (a) within the substrate;
   (b) within the multiplicity of spaces defined by the unbranched alkyl molecules; and
   (c) within the substrate and within the multiplicity of spaces defined by the unbranched alkyl molecules.

7. The device of claim 6, wherein the multiplicity of drug molecules is disposed within the multiplicity of spaces defined by the unbranched alkyl molecules.

8. The device of claim 6, wherein said multiplicity of drug molecules comprises molecules of more thanone type of drug.

9. The device of claim 6, wherein said drug is selected from the group of drugs consisting of insulin, estrogens, androgens, hypnotics, antipsychotics, narcotics and diuretics.

10. The device of claim 1 further comprising a multiplicity of effector molecules wherein each member of the multiplicity of effector molecules is covalently attached to the distal end of a $C_{10}$ to $C_{22}$ unbranched alkyl molecule of the surface layer.

11. The device of claim 10, wherein the effector molecule is selected from the group of effector molecules consisting of protein, lipid, carbohydrate, nucleic acid and peptide.

12. The device of claim 1, wherein the device is an implantable medical device.

13. The device of claim 2, wherein the device is an implantable medical device.

14. The device of claim 1 or claim 2, wherein the ordered state of the surface layer forms a crystalline layer characterized by Fourier Infrared Peak Frequencies at 2850+/−2 cm$^{-1}$ and 2920+/−2 cm$^{-1}$.

15. A method of making a biomedical device comprising a surface layer, said method comprising the steps of:
 (a) disposing a multiplicity of drug molecules within a polymeric or hydrogel substrate; and
 (b) covalently attaching a multiplicity of $C_{10}$ to $C_{22}$ unbranched alkyl molecules to the surface of the substrate by forming a covalent linkage between an end group on each member of the multiplicity of $C_{10}$ to $C_{22}$ unbranched alkyl molecules and a reactive group on the substrate, thereby forming a surface layer on the substrate wherein:
  (1) the multiplicity of alkyl molecules define a multiplicity of spaces therebetween;
  (2) each member of the multiplicity of alkyl molecules possesses a proximal end and a distal end, the proximal end being covalently linked to the substrate; and
  (3) the surface layer has an ordered state and a less ordered state, the surface layer being reversibly convertible to the less ordered state from the ordered state in response to an effective amount of sound or thermal energy.

16. A method of delivering a drug to a subject, said method comprising the steps of:
 (a) introducing into a subject a device comprising:
  (1) a polymeric or hydrogel substrate comprising a multiplicity of drug molecules; and
  (2) a surface layer comprising a multiplicity of $C_{10}$ to $C_{22}$ unbranched alkyl molecules, wherein:
   (i) the multiplicity of alkyl molecules define a multiplicity of spaces therebetween;
   (ii) a multiplicity of drug molecules are disposed within said spaces;
   (iii) each member of the multiplicity of alkyl molecules possesses a proximal end and a distal end, the proximal end being covalently linked to the substrate; and
   (iv) the surface layer has an ordered state and a less ordered state, the surface layer being reversibly convertible to the less ordered state from the ordered state in response to an effective amount of sound or thermal energy; and
 (b) subjecting the device to an amount of sound or thermal energy effective to induce release of the drug molecules from the surface layer.

17. The method of claim 16, wherein the device is subjected to sound energy having a frequency in the range of from 20 kHz to 100 kHz for a period of from 1 minutes to 10 minutes.

* * * * *

UNITED STATES PATENT AND TRADEMARK OFFICE
CERTIFICATE OF CORRECTION

PATENT NO. : 6,444,217 B1
DATED : September 3, 2002
INVENTOR(S) : C.S.-K. Kwok et al.

It is certified that error appears in the above-identified patent and that said Letters Patent is hereby corrected as shown below:

Title page,
Item [56], References Cited, OTHER PUBLICATIONS, "Kwok, C.S. et al." reference, "et al," should read -- et al., --
"Maoz R. et al." reference, "eta 1.," should read -- et al., --
"*Biosens, Bioelectron.*, 19:785:88" should read -- *Biosens., Bioelectron.*, 10:785-88 --
Item [57], ABSTRACT,
Line 2, after "delivery devices" insert -- , --
Item [74], *Attorney, Agent, or Firm*, after "O'Connor" delete ";"

Column 2,
Line 2, "a proreactive chemical groups" should read -- proreactive chemical groups --
Line 4, "groups permits" should read -- groups permit --

Column 4,
Line 44, after "includes drug" delete "a"
Line 48, no paragraph break after "molecules 18."

Column 6,
Line 9, "2850+/2" should read -- 2850+/-2 --

Column 7,
Line 25, "$C_{10}$ $_{to}$ $_{C22}$" should read -- $C_{10}$ to $C_{22}$ --

Column 9,
Line 44, "($C_2$" should read -- ($C_{12}$ --
Line 55, after "1.5 g" insert -- ) --
Line 56, "15%sodium" should read -- 15% sodium --
Line 65, "1day." should read -- 1 day. --

UNITED STATES PATENT AND TRADEMARK OFFICE
CERTIFICATE OF CORRECTION

PATENT NO. : 6,444,217 B1
DATED : September 3, 2002
INVENTOR(S) : C.S.-K. Kwok et al.

It is certified that error appears in the above-identified patent and that said Letters Patent is hereby corrected as shown below:

Column 10,
Line 37, "A1 $K_{1,2}$" should read -- A1 $K_{\alpha 1,2}$ --
Line 62, "$10^{-9}$Torr" should read -- $10^{-9}$ Torr --

Column 11,
Line 8, "(m/z85$^-$)" should read -- (m/z 85$^-$) --
Line 8, "$C_{13}H_{26}NO2^-$" should read -- $C_{13}H_{26}NO^{2-}$ --
Line 41, after "(i.e." insert -- , --
Line 49, after "substrate 12." begin a new paragraph Column 12,
Line 23, "30 min." should read -- 30 min. --
Line 67, "min )." should read -- min). --

Column 13,
Line 24, "$cm^{-1}$was" should read -- $cm^{-1}$ was --
Line 27, "cm-1 )" should read -- cm-1) --
Line 30, "approximations. The" should read -- approximations, the --
Lines 38 and 39, "cm-1" should read -- $cm^{-1}$ --

Column 14,
Line 3, "min )," should read -- min), --
Line 7, "min," should read -- min, --
Line 37, "g/cm 3)" should read -- $g/cm^3$) --
Line 50, after "structure, within" insert -- substrate 12 close to substrate --
Line 56, "min )." should read -- min). --

Column 15,
Line 34, "mV))" should read -- mV) --

UNITED STATES PATENT AND TRADEMARK OFFICE
CERTIFICATE OF CORRECTION

PATENT NO. : 6,444,217 B1
DATED : September 3, 2002
INVENTOR(S) : C.S.-K. Kwok et al.

It is certified that error appears in the above-identified patent and that said Letters Patent is hereby corrected as shown below:

Column 16,
Line 54, "thanone" should read -- than one --

Signed and Sealed this

Sixth Day of July, 2004

JON W. DUDAS
*Acting Director of the United States Patent and Trademark Office*